United States Patent [19]

Lundbäck

[11] Patent Number: 5,630,855

[45] Date of Patent: May 20, 1997

[54] MOISTURE-COLLECTING DEVICE

[75] Inventor: Stig Lundbäck, Vaxholm, Sweden

[73] Assignee: Humanteknik AB, Stockholm, Sweden

[21] Appl. No.: 416,826

[22] PCT Filed: Oct. 13, 1993

[86] PCT No.: PCT/SE93/00837

§ 371 Date: Jun. 21, 1995

§ 102(e) Date: Jun. 21, 1995

[87] PCT Pub. No.: WO94/08636

PCT Pub. Date: Apr. 28, 1994

[30] Foreign Application Priority Data

Oct. 16, 1992 [SE] Sweden ................................ 9203046

[51] Int. Cl.⁶ .................................................. B01D 53/26
[52] U.S. Cl. .................... 55/215; 55/332; 55/486; 55/528; 96/154
[58] Field of Search ........................... 55/212, 215, 274, 55/275, 332, 333, 486, 527, 528; 95/117, 118; 96/154; 604/358, 361, 372, 378, 379

[56] References Cited

U.S. PATENT DOCUMENTS

| 3,147,097 | 9/1964 | Aguas | 55/486 X |
|---|---|---|---|
| 3,248,859 | 5/1966 | Stephenson et al. | 55/486 X |
| 3,300,949 | 1/1967 | Smylie et al. | 95/117 |
| 3,309,843 | 3/1967 | Rigopulos et al. | 95/117 |
| 3,410,057 | 11/1968 | Lerner | 55/528 X |
| 3,499,270 | 3/1970 | Paugh | 55/527 X |
| 3,521,429 | 7/1970 | Leffler | 55/527 X |
| 3,620,677 | 11/1971 | Morison | 55/274 X |
| 4,465,485 | 8/1984 | Kashmer et al. | 55/215 X |
| 4,469,598 | 9/1984 | White | 55/486 X |
| 4,784,892 | 11/1988 | Storey et al. | 55/527 X |
| 4,902,449 | 2/1990 | Hobbs | 55/528 X |
| 5,141,794 | 8/1992 | Arroyo | 604/372 X |
| 5,147,646 | 9/1992 | Graham | 604/372 X |
| 5,151,251 | 9/1992 | Solcia et al. | 55/274 X |
| 5,294,407 | 3/1994 | Succi et al. | 55/274 X |
| 5,298,046 | 3/1994 | Peisert | 55/525 X |
| 5,395,411 | 3/1995 | Kobayashi | 55/486 |

FOREIGN PATENT DOCUMENTS

| 0390094 | 10/1990 | European Pat. Off. . |
|---|---|---|
| WO92/10220 | 6/1992 | WIPO . |

*Primary Examiner*—Robert Spitzer
*Attorney, Agent, or Firm*—Hill, Steadman & Simpson

[57] ABSTRACT

A moisture-collecting device comprises an enclosure (12) with a fluid inlet (15), a fluid outlet (16) and a fluid passage (18) extending between the fluid inlet and the fluid outlet, and a moisture-absorbing body (17) disposed in the fluid passage. The moisture-absorbing body fills substantially the entire flow cross section of the fluid passage (18) and to a substantial degree consists of a material having a high moisture-absorbing capability. The moisture-absorbing body defines, or has formed within it, at least one fluid passageway (19) which is in fluid flow communication with the fluid inlet (15) and the fluid outlet (16) and is substantially free of moisture-absorbing material. When the moisture-absorbing body (17) absorbs moisture it swells, and when it has swelled to a predetermined extent it may actuate a control or operating member, such as a valve.

24 Claims, 3 Drawing Sheets

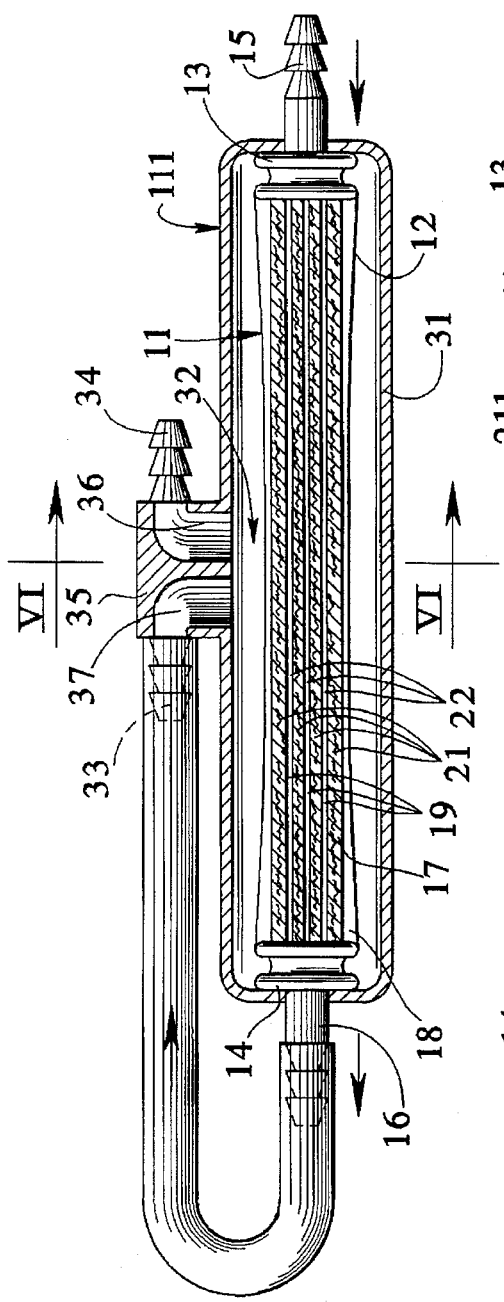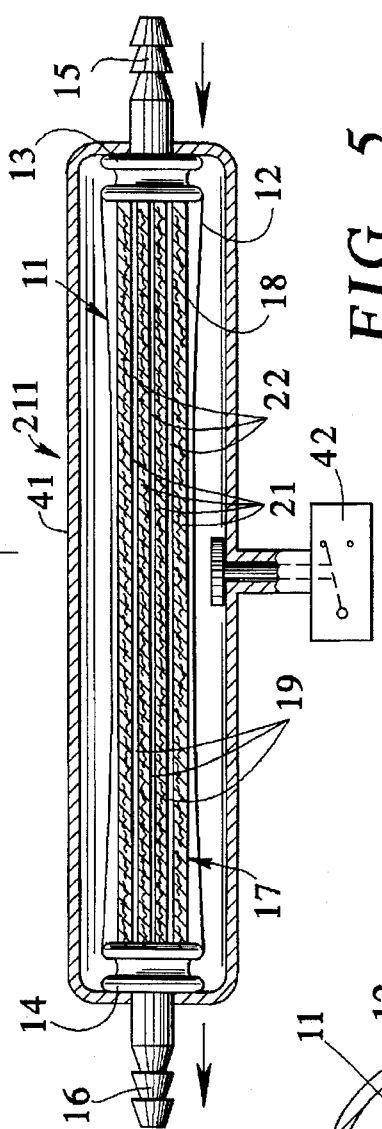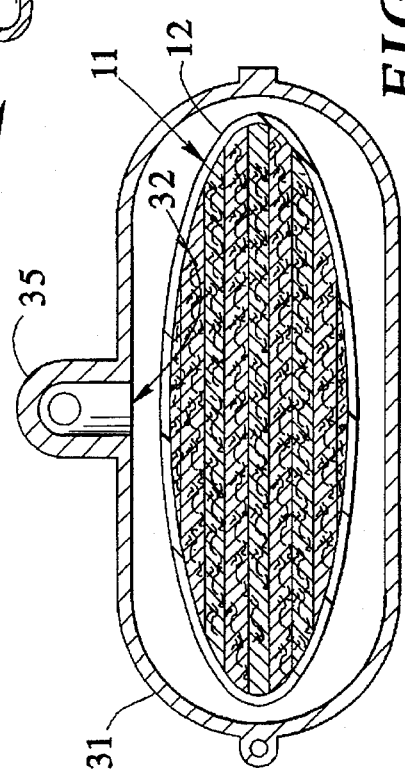

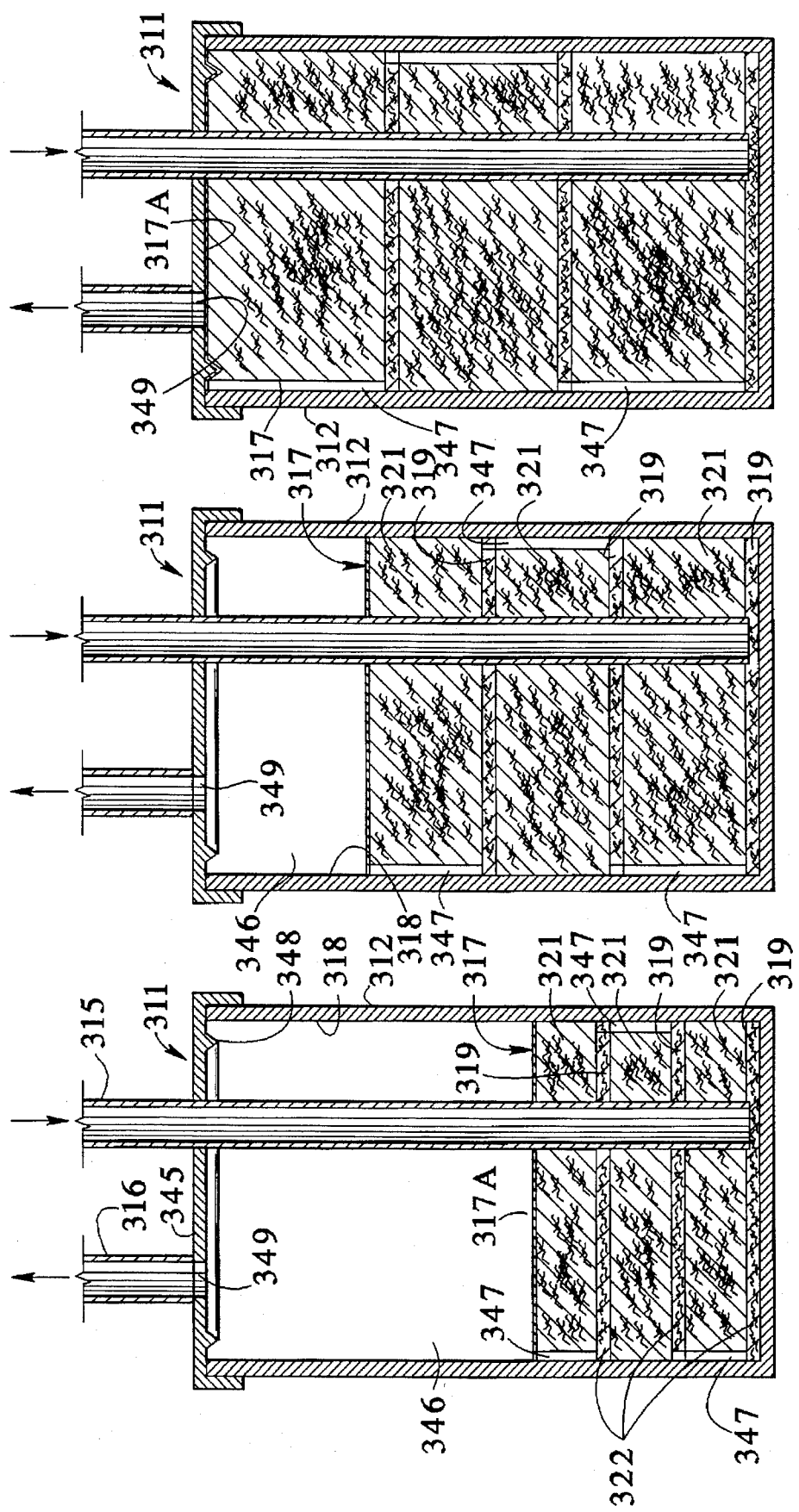

MOISTURE-COLLECTING DEVICE

This invention relates to a moisture-collecting device of the kind which comprises, firstly, an envelope having a fluid inlet, a fluid outlet and a fluid passage which extends between the fluid inlet and the fluid outlet, and, secondly, a moisture-collecting means which is disposed in the fluid passage of the envelope.

Many different embodiments of devices of this kind are known. An embodiment which is often used in the nursing of patients comprises a rigid vessel which can be closed so as to be airtight and forms the envelope, and a bag-like container which is connected with the fluid inlet and serves as the moisture-collecting means. In use of this embodiment of the device, the fluid outlet is connected with a vacuum pump or other vacuum source while the fluid inlet is connected with, for example, a catheter or the like which is inserted in the respiratory tract of a patient to aspirate phlegm.

Phlegm or other more or less liquid substances which are transported through the fluid inlet are allowed to flow into the bag under the action of the vacuum that is maintained in the vessel and communicated with the inlet through one or more openings in the bag, which is attached to and suspended from the inlet. After use, the bag is detached and thrown away to be replaced by a new bag.

With proper positioning and use of this known device, phlegm drawn into the inlet is prevented from reaching the outlet and the hose that connects the fluid outlet with the vacuum source, and also from contaminating the interior surfaces of the vessel. However, the device is bulky and cumbersome.

An object of the invention is to provide a device of the above-indicated kind which lends itself to a simple and inexpensive construction and which is easy to use.

To this end, the device according to the invention is constructed as set forth in the independent claim. Characterising features of preferred embodiments are set forth in the dependent claims and the following exemplifying description of the device according to the invention.

As explained in greater detail below, in the device according to the invention the moisture-collecting means comprises a moisture-absorbing body, a substantial portion of which is comprised of a material having large moisture-absorbing capability and which is disposed in the envelope in such a way that the fluid flowing through the envelope, such as aspirated air and liquid or gaseous moisture that is transported with the air, will be brought in a moisture-surrendering relation with the moisture-absorbing body. For practical purposes, therefore, fluid flowing through the envelope cannot reach the fluid outlet without having been brought so close to the moisture-absorbing material that at least the liquid phase, if any, of the fluid will be taken up by this material.

Three exemplary embodiments of the device according to the invention, which have been chosen to illustrate the invention, will be described in greater detail below with reference to the accompanying drawings.

FIG. 4 shows a second embodiment, namely an absorber unit which incorporates the first embodiment, in a view corresponding to FIG. 2;

FIG. 5 shows a modification of the embodiment in FIG. 4;

FIG. 6 shows a cross-section taken on line VI—VI in FIG. 4;

FIGS. 7 to 9 are vertical sectional views of a third embodiment shown in three different conditions.

Figure 1:
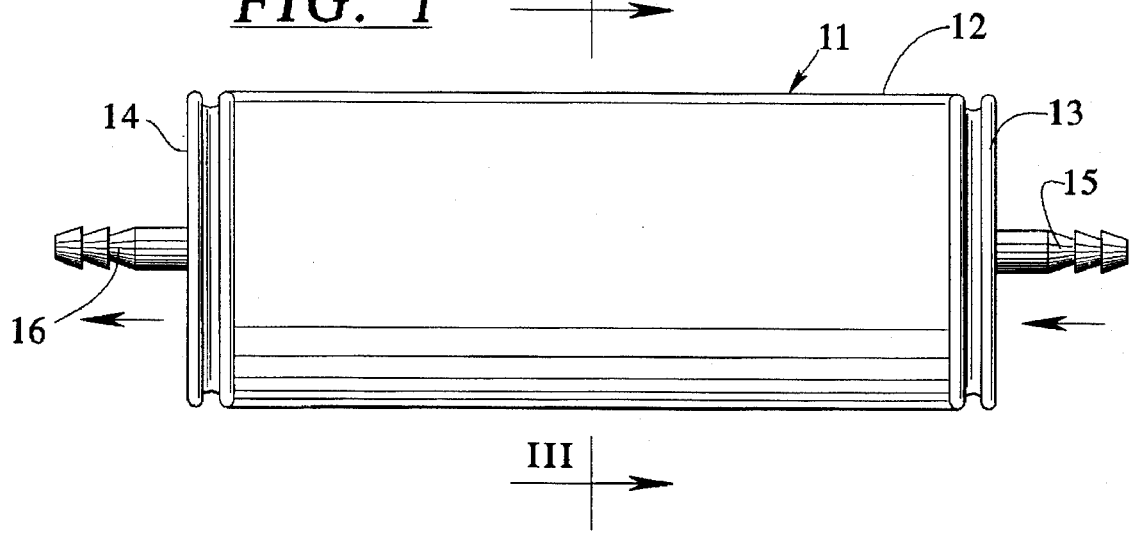
FIGS. 1 to 3 show a first embodiment in respectively plan view, elevation (partly in longitudinal section), and cross-section taken on line III—III in FIG. 1.
Figure 2:
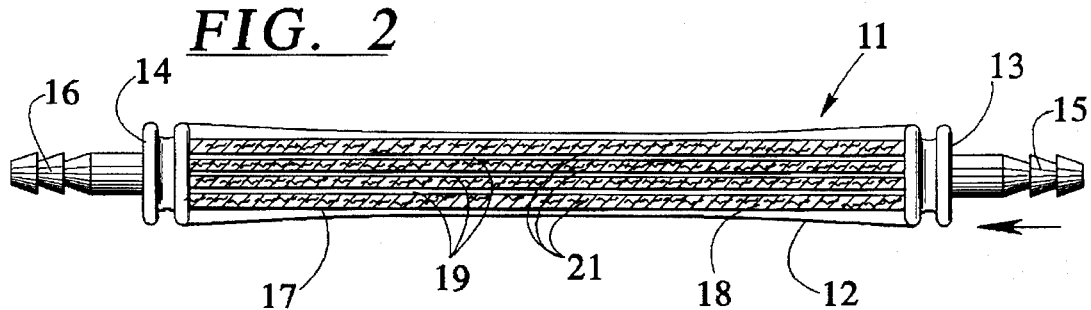
Figure 3:
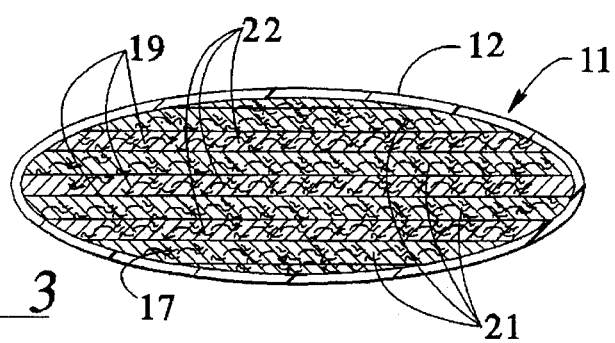

As shown in FIGS. 1–3, the moisture-collecting device, hereinafter referred to as a moisture-absorbing unit, is intended for use as a disposable item and comprises an envelope 11, which is formed of a tubular member 12 made of a plastic film or other flexible sheet material that is impervious to gases and liquids, and a pair of rigid end pieces 13 and 14 with which the ends of the plastic tubular member 12 are connected in airtight fashion and which are integrally formed with respectively a tubular inlet connector 15 and a tubular outlet connector 16. Moreover, the moisture-absorbing unit comprises a laminated, elongate moisture-absorbing body 17 which is disposed in the plastic tubular member 12. The moisture-absorbing body occupies substantially the entire space 18 which is defined by the tubular member 12 and the opposing sides of the end pieces 13, 14 and which forms a fluid passage extending between the inlet and outlet connectors 15, 16.

As is explained in greater detail below, the moisture-absorbing body 17 is provided with a plurality of longitudinal fluid flow-through passageways 19 which extend between the opposite ends of the body and are distributed over substantially the entire cross-section thereof. In order that fluid may easily flow between the end pieces 13, 14 through all of these passageways in the moisture-absorbing body 17, each end piece is formed with a large number of openings which are distributed over the entire end piece surface facing the moisture-absorbing body and communicate with the bore of the associated tubular connector 15, 16.

The moisture-absorbing body 17 is made up of a number of layers 21 of a material that is highly absorbing to moisture and swells or expands in response to uptake of moisture. Preferably, the material is a so-called superabsorbent or comprises a superabsorbent as an essential constituent material thereof; superabsorbents are common constituent materials in diapers, sanitary napkins and other products which have to possess high liquid-absorbing capability. The layers 21 are separated by interleaved intermediate layers 22 which are permeable to air and liquids and define the passageways 19. Preferably, these intermediate layers are made up of a material which has no or only a week tendency to absorb liquid; the material preferably is hydrophobic. For example, the intermediate layers 22 may be formed from woven or nonwoven fabrics of hydrophobic filaments or fibres. They should be sufficiently firm to prevent the passageways 19 from collapsing in use of the moisture-collecting device.

The intermediate layers 22 and the passageways 19 they define between adjacent moisture-absorbing layers 21 serve to allow liquid and air to flow between the absorbing layers 21 under the influence of a pressure differential between the inlet end piece 13 and the outlet end piece 14 even when the absorbing layers 21 have lost, as a consequence of absorption of moisture, their ability to pass liquid or air.

When the device shown in FIGS. 1 to 3 is used, e.g. in an application of the nature described initially, the inlet connector 15 is connected with a vacuum pump or other vacuum source (not shown) and the inlet connector 15 is connected with the site from which liquid is to be drawn. The vacuum that then develops inside the envelope 11 causes the tubular member 12 to be drawn against the moisture-absorbing body 17, but even if, as a consequence, the moisture-absorbing body should be compressed to some extent, air will not be prevented from passing through the moisture-absorbing body.

Initially, the air can pass relatively easily, not only through the passageways 19 but also through the moisture-absorbing layers 21 because these are initially, when completely dry, permeable to air. As liquid entrained by the aspirated air enters the moisture-absorbing body 17, this liquid is collected and thus retained by the absorbing layers 21. Consequently, only the aspirated air can flow on and pass through the outlet connector 16. The absorption of the liquid causes the layers 21 progressively to lose their permeability to air, but the passageways 19 always ensure that additional liquid can be drawn into the moisture-absorbing body 17 and become absorbed.

With increased amount of absorbed liquid, the moisture-absorbing body 17 will swell or expand and, consequently, expand the tubular member 12. This expansion is particularly forceful if a so-called superabsorbent is used in the moisture-absorbing body. However, the expansion will not adversely influence the absorption capability or the permeability of the passageways 19 to any substantial degree; the collection of liquid can continue until the entire moisture-absorbing body 17 is filled with liquid up to the limit of its absorption or expansion capability.

FIGS. 4 to 6 show two variants 111 and 211 of an absorber unit, designated by 111 in FIGS. 4 and 6 and by 211 in FIG. 5, which embodies the invention and incorporates the moisture-absorbing unit shown in FIGS. 1 to 3 and additionally comprises a rigid housing or outer enclosure 31 and 41, respectively, and a control or actuating member 32 and 42, respectively, associated therewith.

In the absorber unit 111 shown in FIGS. 4 and 6, the outer enclosure 31 is fluidtight, i.e., like the envelope 11 it is impervious to gases and liquids, and it is also sealed to the tubular inlet and outlet connectors 15, 16 of the absorbing device 11. One side wall of the outer enclosure 31 is provided with a pair of additional tubular connectors 33 and 34 on a lug 35. As is best shown in FIG. 4, the passages of these connectors communicate with one another by way of openings 36 and 37 in the lug 35 and said one side wall of the outer enclosure 31.

The tubular connector 33 is adapted to be connected with the tubular outlet connector 16 as is shown in FIG. 4, and the tubular connector 34 is adapted to be connected with the vacuum source. The tubular inlet connector 15 is adapted to be connected in the manner described with reference to FIGS. 1 to 3.

In use of the absorber unit shown in FIGS. 4 and 6, the interior of the outer enclosure 31 and the interior of the tubular member 12 are at substantially the same pressure. Consequently, the moisture-absorbing body 17 is not compressed by the ambient pressure in the manner described above with reference to FIGS. 1 to 3. Instead, the outer enclosure 31 will be subjected to an outer overpressure and it of course has to be constructed so as to be able to withstand that overpressure.

As moisture is being absorbed, the moisture-absorbing body 17 gradually swells or expands, and when a certain amount of moisture, i.e., the maximum amount of moisture it is desired to charge the moisture-absorbing body 17 with, has been absorbed and the moisture-absorbing body 17 has thereby expanded to a certain degree, one side of the tubular member 12 will engage the inner side of the side wall of the outer enclosure 31 and, consequently, will cover and close the openings 36 and 37. As a consequence, vacuum can no longer be communicated from the source of vacuum to the moisture-absorbing unit. This state can readily be detected and indicated in any suitable manner known per se so that the attention of the operator or attending person is directed to the necessity of taking appropriate action, such as replacement of the moisture-absorbing unit with a new one.

As is apparent from the foregoing description and from FIGS. 4 and 6, openings 36 and 37 jointly with the tubular member 12 form a shut-off valve 32 the closing of which renders the moisture-absorbing unit inoperative and triggers a signal that indicates the inoperative condition of the unit.

In the embodiment of FIGS. 4 and 6 the fluid outlet of the tubular member 12 enclosing the moisture-absorbing body 17 may also be "distributed" throughout or over a large portion of the surface of the moisture-absorbing body, for example in that the tubular member 12 is formed from a semipermeable membrane, that is, a material which is permeable to gas but impermeable to liquid. In such case it may be necessary to provide air passageways in a suitable manner around the moisture-absorbing body 17, between the absorbing material and the gas-permeable tubular member 12, e.g. by means of ridges or other spacing means, such as means similar to the non-absorbing layers 19.

In the absorber unit 211 shown in FIG. 5, the housing or outer enclosure 41 is provided with a control means in the form of a switch 42 which is operated (opened or closed) when the moisture-absorbing unit has expanded to a certain predetermined degree. Switch 42 may be used to produce an alarm or indicating signal, for example. The outer enclosure 41 need not be sealed or enclose the moisture-absorbing unit completely. For example, it may be open on one side so that the moisture-absorbing unit can readily be inserted in and removed from the outer enclosure.

Naturally, a switch corresponding to switch 42 may also be provided in the absorber unit 111 shown in FIGS. 4 and 6, and it is also possible in the asorber unit 211 shown in FIG. 5 to arrange for the outer enclosure 42 to be at the same pressure as the interior of the moisture-absorbing unit as described with reference to FIG. 4.

In the absorber unit 311 shown in FIGS. 7–9 the moisture-absorbing body 317 is contained in a rigid, sealed housing or envelope 312 having a removable cover 345. This cover is provided with an inlet conduit 315, which reaches down to a level close to the bottom of the envelope 312, and an outlet conduit or tubular outlet connector 316.

In this embodiment as well, the moisture-absorbing body 317 is laminated or layered, but here the absorbing layers 321 are horizontal, disposed transversely of the general or main flow-through direction (vertical) of the flow passage 318 formed by the envelope 312 between the opening of the inlet conduit 315 and the tubular outlet connector 316.

As in the foregoing embodiments, the absorbing layers are separated by non-absorbing, e.g. hydrophobic, horizontal intermediate layers 322 which define horizontal passageways 319. Such a passageway-defining layer 319 is also provided beneath the lowermost absorbing layer 321 and communicates with the opening of the inlet conduit 315. The passageways 319 are in fluid flow communication with one another and with the initially empty space 346 above the uppermost absorbing layer 321 through the intermediary of vertical passageways 347 provided at opposite sides of the envelope 312 such that the aspirated air flows in a zigzag path from the inlet conduit 315 to the just-mentioned space 346, namely to the extent that it cannot flow through the absorbing layers 319. Moisture transported with the aspirated air can then readily be taken up by the absorbing layer or layers 321 which border(s) on the air passageway 322 or 347 being considered.

As in the embodiment shown in FIGS. 4 and 6, the moisture-absorbing body 317 will be expanded gradually as it takes up moisture (FIG. 8), and finally it will engage and close the opening 349 of the tubular outlet connector 316 so that the device will be rendered inoperative because vacuum can no longer be maintained within the envelope 312 (FIG. 9).

On its upper side, the moisture-absorbing body 317 is provided with an impermeable flexible layer 317A at least over the area which confronts the opening 349.

An annular ridge 348 on the underside of the cover 345 encircles the opening 349 and serves to prevent the moisture-absorbing body 317 from closing the opening 399 unintentionally, should the moisture-absorbing body engage the cover 345 only lightly, such as under a force substantially lighter than that which is exerted as a result of full expansion of the moisture-absorbing body upon absorption of moisture.

Although it is preferred to use a laminated or layered moisture-absorbing body as shown to ensure that gas can pass through the moisture-absorbing body in moisture-surrendering relation therewith even after a smaller or larger amount of moisture has been absorbed, it is not essential according to the invention to use such a moisture-absorbing body. The moisture-surrendering relation can be ensured in other ways, e.g. by making the absorbing material in the shape of balls or other discrete bodies which when brought in engagement with one another form open spaces jointly forming a system or network of interstices distributed throughout the moisture-absorbing body. This system or network of interstices may then serve as a passage system through which gas may flow from one side of the moisture-absorbing body to the other in contact with the absorbing material.

I claim:

1. A moisture-collecting device, comprising
   an envelope having a fluid inlet, a fluid outlet and a fluid passage which extends between the fluid inlet and the fluid outlet, and
   a moisture-collecting means which is disposed in the fluid passage of the envelope,
   characterized in that
   the moisture-collecting means is a moisture-absorbing body a substantial constituent portion of which is a material having a high moisture-absorbing capability, and
   the moisture-absorbing body defines or has formed within it, at least one fluid passageway which is in fluid flow communication with the fluid inlet and fluid outlet and is substantially free of moisture-absorbing material.

2. A device according to claim 1, characterized in that the moisture-absorbing body comprises a plurality of moisture-absorbing layers separated by interleaved layers of a fluid-permeable material which is non-absorbent to fluid, said interleaved layers of non-absorbent material defining said fluid passageway or passageways.

3. A device according to claim 1 or 2, characterized in that the fluid passageway or passageways extend substantially in the main or general direction of the fluid passage.

4. A device according to claim 1 or 2, characterized in that the fluid passageway or passageways extend substantially transversely to the main or general direction of the fluid passage.

5. A device according to claims 1 or 2, characterized in that the envelope is enclosed in a rigid housing.

6. A device according to claim 5, characterized in that the housing is impervious to fluid and its interior is in open communication with the fluid outlet.

7. A device according to claim 5, characterized in that the fluid passageway or passageways extend substantially in the main or general direction of the fluid passage.

8. A device according to claim 5, characterized in that the fluid passageway or passageways extend substantially transversely to the main or general direction of the fluid passage.

9. A device according to claim 5, characterized by a control member which is operable in response to expansion of the moisture-absorbing body.

10. A device according to claims 1 or 2, characterized by a control member which is operable in response to expansion of the moisture-absorbing body.

11. A device according to claim 10, characterized in that the material having a high moisture-absorbing capability, or a constituent of said material, is a material which swells in response to moisture uptake.

12. A device according to claims 1 or 2, characterized in that the envelope is rigid.

13. A device according to claims 1 or 2, characterized in that the material having a high moisture-absorbing capability, or a constituent of said material, is a material which swells in response to moisture uptake.

14. A device according to claims 1 or 2, characterized in that the moisture-absorbing body comprises a substantial amount of a superabsorbent.

15. A device according to claims 1 or 2, characterized in that the envelope is impervious to gases and liquids.

16. A device according to claims 1 or 2, characterized in that the moisture-absorbing body substantially fills the cross-section of the envelope.

17. A moisture-collecting device, comprising:
    an envelope having a fluid inlet, and a fluid outlet;
    a moisture absorbing body composed of a material having a high moisture-absorbing capability, arranged within said envelope; and
    at least one fluid passageway within said envelope which is in fluid flow communication with said fluid inlet and said fluid outlet, substantially free of moisture-absorbing material, but exposing fluid flowing in said passageway to said moisture-absorbing body.

18. A device according to claim 17, wherein said moisture-absorbing body comprises a plurality of moisture-absorbing layers separated by interleaved layers of a fluid-permeable material which is non-absorbent to fluid, said interleaved layers of non-absorbent material defining said fluid passageway.

19. A device according to claim 17, wherein said fluid passageway extends linearly from said fluid inlet toward said fluid outlet.

20. A device according to claim 17, wherein said fluid passage way extends in serpentine fashion between said inlet and said outlet.

21. A device according to claim 17, further comprising a rigid housing surrounding said envelope.

22. A device according to claim 21, wherein said housing is impervious to fluid and an interior of said housing is an open communication with said fluid outlet.

23. A device according to claim 17, wherein said moisture absorbing body comprises a material which swells in response to moisture absorption, said moisture absorbing body having a surface which upon a preselected degree of swelling closes said outlet.

24. A device according to claim 17, further comprising a control member having a surface portion arranged within said envelope, and said moisture absorbing body is composed of a material which swells in response to moisture absorption, and said moisture absorbing body having an actuation portion aligned to press against said surface portion of said control member, said control member activated by pressing of said surface portion by said actuation portion of said moisture absorbing body when said body swells to a preselected amount.

* * * * *